Figure 5:
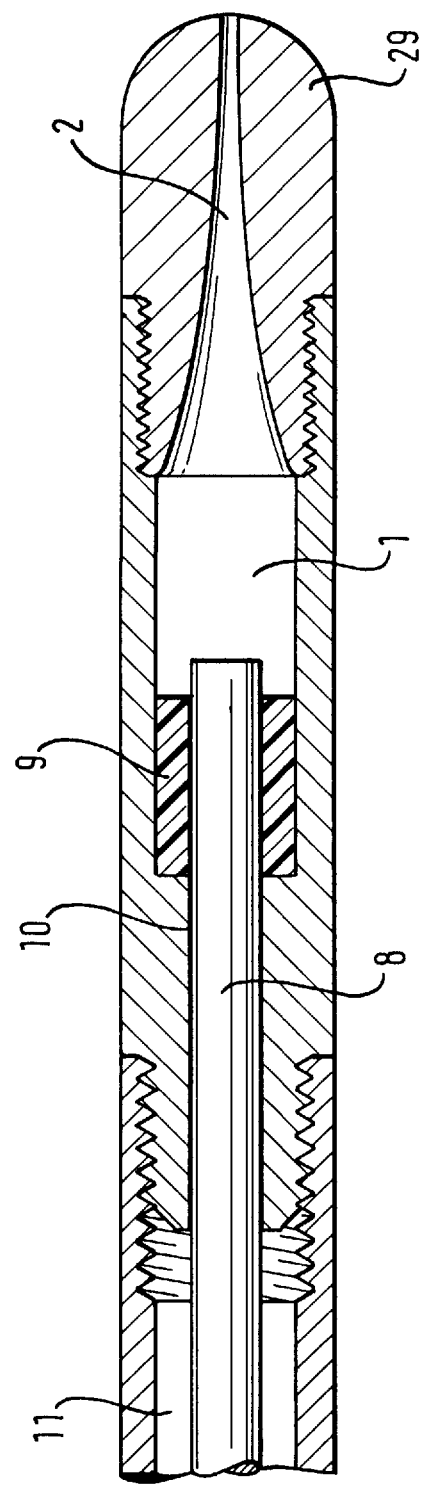

United States Patent [19]
Menne et al.

[11] Patent Number: 5,840,061
[45] Date of Patent: Nov. 24, 1998

[54] EJECTION APPARATUS FOR THE HIGH PRESSURE EJECTION OF A LIQUID

[75] Inventors: Andreas Menne, Meersburg; Wolfgang Merkle, Linnich; Manfred Schulz, Oberlingen, all of Germany; Denis Klopfenstein, Morges, Switzerland

[73] Assignee: Ferton Holding, Delemont, Switzerland

[21] Appl. No.: 765,790

[22] PCT Filed: May 14, 1996

[86] PCT No.: PCT/EP96/02072

§ 371 Date: Jan. 15, 1997

§ 102(e) Date: Jan. 15, 1997

[87] PCT Pub. No.: WO96/36381

PCT Pub. Date: Nov. 21, 1996

[30] Foreign Application Priority Data

May 15, 1995 [DE] Germany ......................... 295 07 987 U

[51] Int. Cl.⁶ .................................................. A61M 5/30
[52] U.S. Cl. ................................................................ 604/68
[58] Field of Search ................................. 604/68, 69, 70, 604/131, 140, 141, 150

[56] References Cited

U.S. PATENT DOCUMENTS

| | | |
|---|---|---|
| 3,490,696 | 1/1970 | Cooley . |
| 3,788,315 | 1/1974 | Laurens .................................... 604/70 |
| 4,596,556 | 6/1986 | Morrow et al. ........................... 604/70 |
| 4,913,699 | 4/1990 | Parsons .................................... 604/68 |
| 5,024,656 | 6/1991 | Gasaway et al. ..................... 604/68 X |
| 5,116,313 | 5/1992 | McGregor . |
| 5,160,336 | 11/1992 | Favre . |
| 5,256,142 | 10/1993 | Colavecchio ............................. 604/68 |
| 5,304,147 | 4/1994 | Johnson et al. ........................ 604/183 |
| 5,569,189 | 10/1996 | Parsons .................................... 604/68 |

*Primary Examiner*—Manuel Mendez
*Attorney, Agent, or Firm*—Griffin, Butler Whisenhunt & Szipl, LLP

[57] ABSTRACT

An ejection apparatus for the high pressure ejection of a liquid. The apparatus has the following elements: (a) a pressure chamber for containing the liquid; (b) an ejection opening communicating between an outside and an inside of the pressure chamber; (c) a working piston displaceable in the pressure chamber from a first position at a beginning of a working stroke to second position at an end of the working stroke, having (1) a first end defining a first volume within the pressure chamber when the working piston is at the first position and displacing a second volume, less than the first volume, when the working piston moves from the first position to the second position, and (2) having a second end distal from the first end; and (d) a drive for driving the working piston including (1) an impact member for elastically impacting the second end of the working piston to cause the working piston from the first to the second position and (2) means for accelerating the impact member to impact the working piston. The device can be constructed either as an endoscopic device for delivering liquids in minimally invasive surgical procedures, or as a needle-less inoculation device.

28 Claims, 4 Drawing Sheets

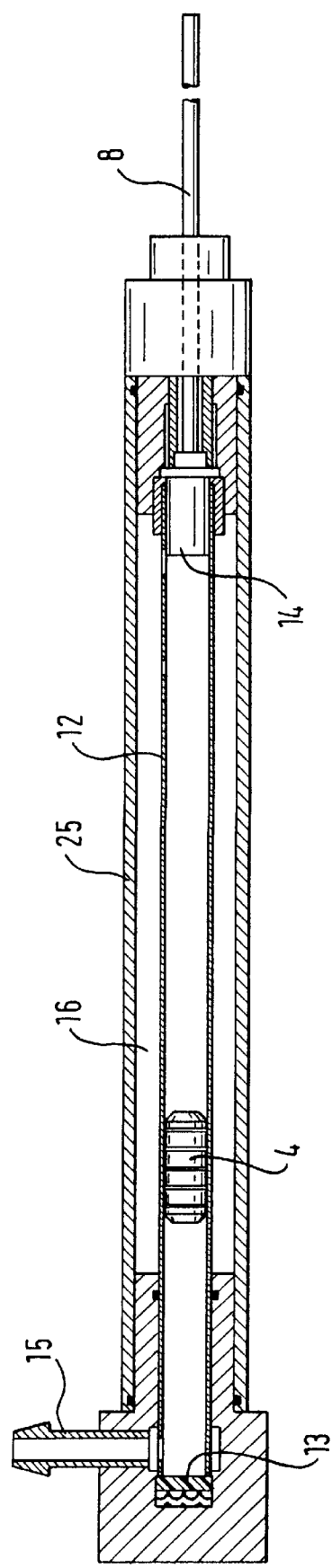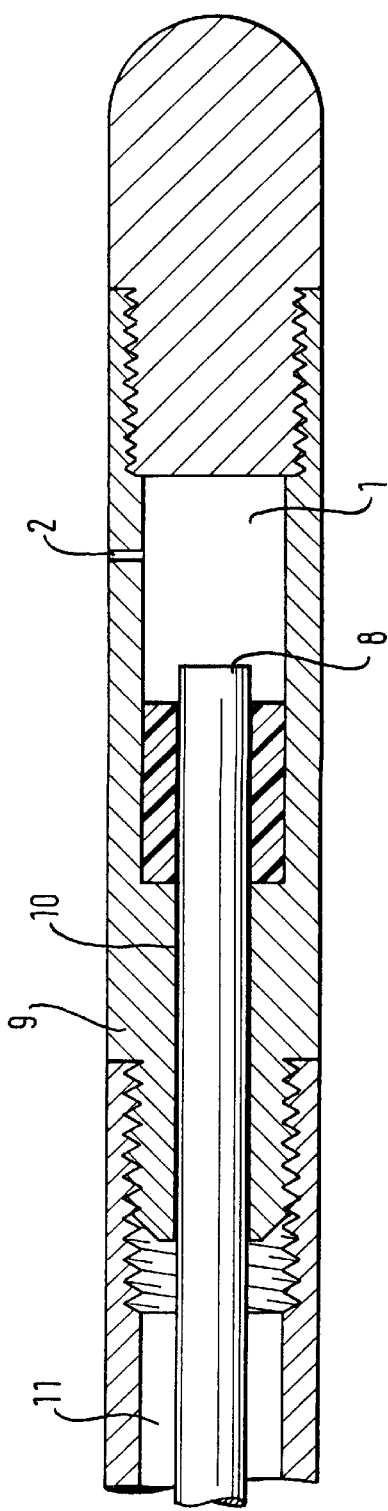

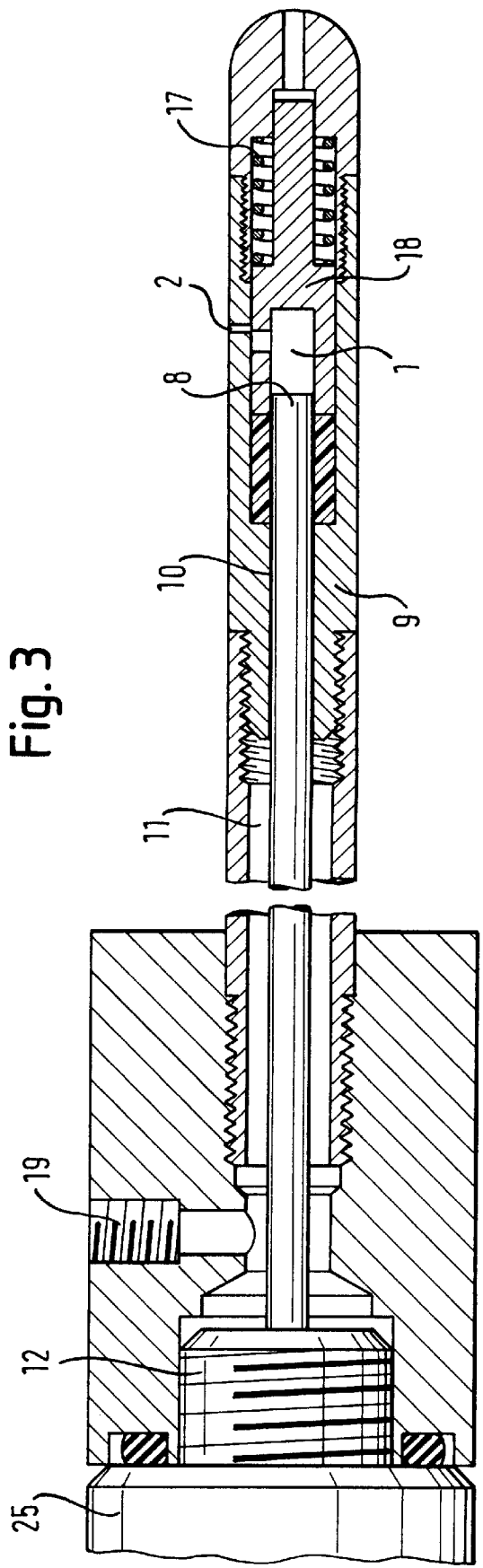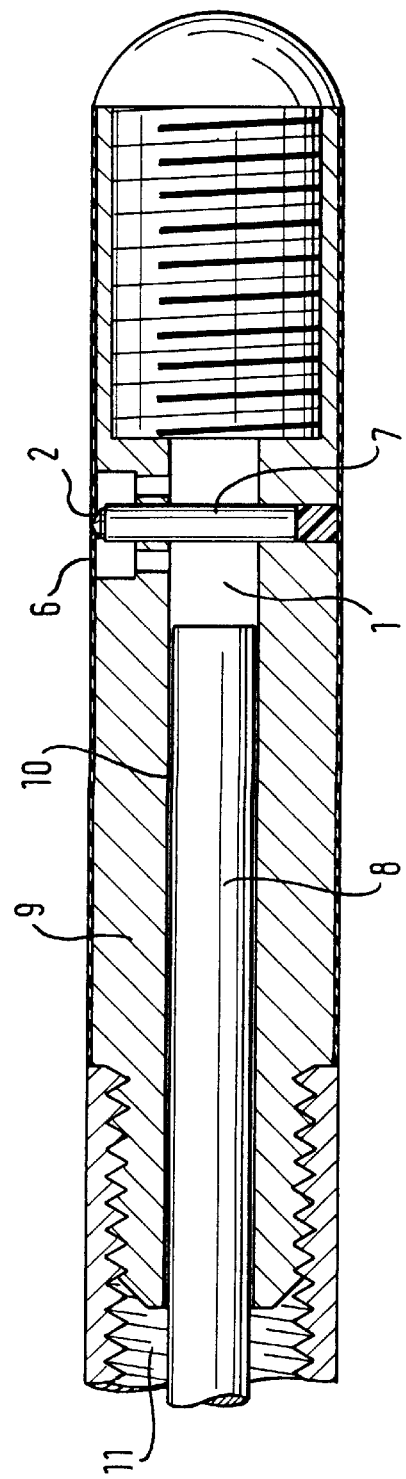

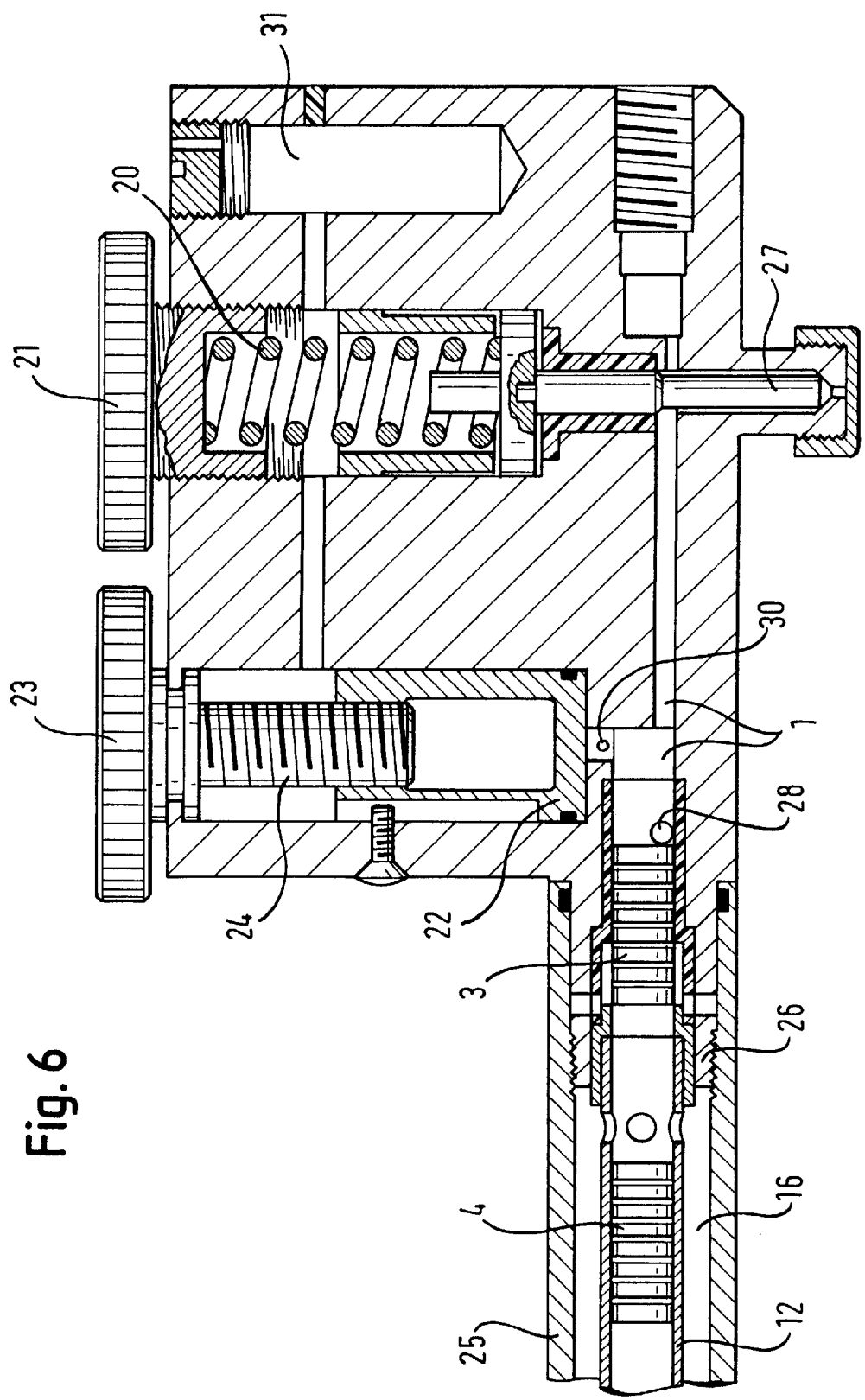

EJECTION APPARATUS FOR THE HIGH PRESSURE EJECTION OF A LIQUID

BACKGROUND OF THE INVENTION

The invention relates to an ejection apparatus for the high-pressure ejection of a liquid or a solid particle-containing-liquid. The ejection apparatus has a pressure chamber for accommodating the liquid. The chamber opens into an ejection opening, and is delimited by a working piston which can be displaced in the chamber by a drive.

In known needle-less inoculation devices, the driving piston is in most cases actuated by a tensioned spring, wherein the driving piston acts upon the liquid with a relatively high pressure and the complete liquid volume present in the pressure chamber is ejected through the ejection opening. It is also known (See for example, GB Patent Specification No. 993 309) that the pressure chamber is formed as an ampoule having deformable walls, wherein a driving piston is used as a drive and to first impart an impact impulse to the working piston, in order to obtain a higher initial ejection pressure and to achieve penetration through the skin, whereafter the working piston is further pushed by a spring arrangement in order to push the rest of the liquid volume out of the ampoule.

The liquid volume generally relates to relatively large quantities in the range of cubic centimeters, which can result in trauma to the tissue surrounding the inoculation location. On the other hand, there is a need for injecting small quantities of liquid in particular cases. Namely, it has been determined that, with a high pressure injection of small quantities of colorants into tissue, the colorant was homogeneously distributed with distinctly less damage to the tissue.

SUMMARY OF THE INVENTION

The present invention solves the problem of how to design an ejection apparatus of the above mentioned type so that small quantities of liquid, in particular cases cubic millimeters, can also be ejected.

According to the invention, this is achieved in that the drive is formed as an impact member exerting an elastic impact on the working piston, which impact member can be accelerated and driven until it elastically impacts the end of the working piston facing away from the pressure chamber, wherein the impact member is not driven with the elastic impact, and the volume of the pressure chamber is larger than the volume of the liquid displaced by the working piston during its working stroke.

As a result of the impact member striking the working piston, an elastic impact is transmitted to the working piston, whereby the working piston transmits a high pressure impulse to the liquid in the pressure chamber which results in high pressure ejection of the liquid from the ejection opening. The ejection pressure and also the ejected liquid volume depend on the impact velocity of the impact member striking the working piston, and can therefore be adjusted by adjusting the driving velocity of the impact member. Since the driving member looses its driving force as a consequence of the elastic impact, only a short impulse is transmitted to the liquid. By means of the short, high pressure impulse transmitted to the liquid in the pressure chamber, a corresponding small quantity of the liquid is ejected from the ejection opening without the total volume of the pressure chamber being emptied. In contrast to the prior art, the impact transmission is only used to eject this small quantity without subsequently ejecting the total volume of the pressure chamber. This is achieved by means of the impact member exerting an elastic impact on the working piston and by the impact transmission, that is due to the transmission of the impulse, the impact member is no longer driven and does not exert any further driving force on the working piston. As a result, it is possible to eject only a small quantity of the liquid in doses.

The volume of the pressure chamber is substantially larger than the displacement volume of the working piston in order to be able eject a small, but dosed quantity of the liquid, independently of the size of the pressure chamber. Preferably, the ratio between the volume of the pressure chamber and the displacement volume of the driving piston is 5:1, particularly 20:1, which ratio can be adjusted by adjusting of the driving velocity of the impact member, that is, the size of the impulse transmitted to the free, movable driving piston.

The lack of drive of the impact member after the transmission of the impulse to the working piston can, for example, be achieved by means of a limit stop by which the impact member is stopped after the transmission of the impulse, or, for example, by means of a corresponding limitation of the time period of the driving impulse acting on the impact member.

The working piston particularly comprises a strong, but preferably elastic and flexible material, in which elastic impact waves are propagated, such as, for example, a metal material. Such a metal material is preferably steel, titanium or a titanium alloy. The impact member can be any component which is driven to strike the working piston, such as, for example, a rocking lever, which is actuated by a driving piston, or, for example, a pivotable flap the end of which strikes the working piston. Preferably, the impact member is formed as a driving piston coaxially aligned with the working piston, which driving piston can be accelerated and driven in a driving pipe.

The impact member can particularly be driven pneumatically, hydraulically, mechanically, electromagnetically, electrostrictively, piezo-electrically or thermally. It is therefore possible to design the actuation of the impact member so that it is driven each time for only one stroke. It is preferred, however, that the impact member can be driven for, controlled, periodic, repeated multiple impact on the driving piston, wherein the impact member and the working piston can be reset in a self-actuated manner. Hereby the total ejected quantity can be adjusted in a controlled manner dependent on the number of the repetitions.

The liquid to be ejected can also be mixed with small solid material particles. Medicaments can, for example, be embedded into carrier particles for the purpose of better dosing, the carrier particles release the well-dosed medicaments in the human body. If such particles or other particles are mixed with the liquid in the pressure chamber, these are also outputted in the ejection process and they behave similarly to the liquid surrounding them. Therefore, using the ejection apparatus a medicament reservoir in the tissue or a deposition of particles for other purposes can be created.

The ejection opening can be open if it is small enough. The ejection opening can thus be formed as a tapering nozzle or as a channel designed to have a volume such that the liquid or air sucked back after an injection remain within the nozzle and do not move into the pressure chamber. By refilling the pressure chamber with fresh liquid, substance located at the outlet end of the nozzle is displaced so that during a subsequent high pressure impulse no sucked-back substances are ejected.

It is however also possible that the ejection opening is regulated by a valve device, which is driven in a controlled manner, or which is preferably activated to open the ejection opening upon a predetermined pressure increase within the pressure chamber, and which can be reset depending on the pressure. It is thus particularly prevented that, when the pressure in the pressure chamber falls under the ambient pressure after the liquid ejection, air or liquid are sucked back into the pressure chamber. The valve device can, for example be a spring loaded valve piston or valve slide. It is particularly also possible that the ejection opening is formed in an elastic membrane delimiting the pressure chamber, and is kept closed, in the rest position of the membrane, by means of the free end of a sealing pin. Thereafter, due to the ejection pressure in the pressure chamber, the membrane is elastically deflected so that the ejection opening is lifted off the free end of the sealing pin and is thereby opened, and along with the decrease of the pressure the ejection opening is again returned to its rest position in which the ejection opening is closed.

For a periodic operation of the device, the pressure chamber comprises an inflow valve which opens in accordance with a pressure decrease in the pressure chamber, so that the pressure chamber is filled again as a result of the decrease of the liquid pressure.

The initial volume of the pressure chamber can also be adjusted. Thereby, the ejection pressure and the duration of the ejection period can be adjusted, since with an increase of the volume of the pressure chamber the ejection pressure is decreased and the ejection period is extended.

A preferred embodiment according to the invention is characterized by the construction as an endoscopic device, wherein the working piston is formed as a long, elastic and flexible probe transmitting elastic impact waves to the liquid in the pressure chamber. From the EP 0 317 507 is known an endoscopic ultrasonic generator in which a driving piston periodically strikes on a probe which transmits elastic impact waves, with which kidney stones can be shattered.

However, in the endoscopic device embodiment according to the invention the working piston can also be short and the pressure chamber can be designed as an elongated liquid-filled channel in the elastic endoscope catheter. The impact wave is thus propagated through the liquid column located in the channel, whereby the endoscope catheter can be designed to be more flexible.

In the ejection apparatus according to the invention, the pressure chamber can be connected to a feed channel of a liquid reservoir, in which a non return valve is disposed blocking flow in the direction toward the liquid reservoir. However, the pressure chamber can also be connected to the liquid reservoir with an inflow channel narrow enough not to significantly diminish the pressure increase in the pressure chamber during the high pressure impulse causing the ejection. For example, in an endoscopic device embodiment of the high pressure ejection apparatus according to the invention, the section of the probe adjacent the pressure chamber is slidably guided in a guiding member, wherein a slit to allow the flow of the liquid is disposed between the guiding member and the probe. The slit opens into a liquid supply channel extending along the probe. The narrow liquid flow-through slit thus forms the inflow valve, since the liquid can only flow through the liquid flow-through slit into the pressure chamber when the pressure in the pressure chamber has decreased again, whereas the short high pressure impulse cannot effect a notable liquid transfer through the narrow flow-through slit. Similarly, any small liquid flow-through opening leading to the pressure chamber is also appropriate as a liquid supply.

Generally, only one ejection opening from the pressure chamber is provided. In one endoscopic device embodiment according to the high pressure ejection apparatus according to the invention it can be advantageous to provide a plurality of ejection openings to, for example, supply a larger area of tissue with ejected inoculation substance.

The invention is elucidated by means of exemplary embodiments, which, at least schematically, are illustrated in the drawings.

BRIEF DESCRIPTION OF THE DRAWINGS

In the drawings:

FIG. 1 shows a preferred embodiment of the driving portion of an ejection apparatus according to the invention;

FIGS. 2 to 5 show four embodiments of the ejection portion of an ejection apparatus according to the invention which is constructed as an endoscopic ejection apparatus, and which is capable of cooperating with the driving portion of FIG. 1; and FIG. 6 shows an embodiment of a high speed injector, which is also capable of cooperating with the driving part of FIG. 1.

DETAILED DESCRIPTION OF THE PREFERRED EMBODIMENTS

In FIG. 1, an embodiment of the driving portion of an injection device according to the invention for the high pressure injection of a liquid is shown. In an accelerator pipe 12, a driving piston 4 is movable back and forward between an exit limit stop 13 at the one end of the pipe and a probe head 14 of a working piston formed as a probe 8 at the other end of the pipe. In this embodiment, the driving piston 4 is driven pneumatically, the compressed air being supplied through a compressed air connection piece 15. Around the accelerator pipe 12, an annular chamber 16 is formed, which is, close to the probe head 14, connected to the interior of the accelerator pipe 12. The driving piston 4 is driven toward the opposite end of the pipe, until it strikes on the probe head 14, by supplying a compressed air pulse to the accelerator pipe 12. The air within the accelerator pipe 12 downstream of the driving piston 4 is displaced to the annular chamber 16 where it is compressed. After supplying the compressed air, the driving piston 4 is driven back within the accelerator pipe 12 by the pressure built-up in the annular chamber 16 until it strikes the exit limit stop 13.

For further details of the driving part of FIG. 1 it is referred to the disclosure of the EP 0 317 507 A1 (U.S. Pat. No. 5,160,336), the disclosure of which is hereby incorporated by reference, in which such a driving part is described in connection with an endoscopic kidney stone shattering device employing the probe 8.

According to the invention, the elongated probe 8 serves as a driving piston for the high pressure ejection of a liquid. Embodiments for an endoscopic ejection apparatus according to the invention are illustrated by FIGS. 2 to 5. A pressure chamber 1 containing liquid and flowing into an ejection opening 2 is delimited by the distal end of the probe 8. According to FIG. 2 the narrow ejection opening 2 is always open; according to FIG. 3 the ejection opening 2 is controlled by a valve device being constructed as a slide valve 18 slidable against the restoring force of a spring 17. According to FIG. 4, the pressure chamber 1 is circumscribed by a membrane 6 in which the ejection opening 2 is formed which, however, in the position of rest of the membrane is closed by the free end of a sealing pin 7.

The distal end section of the probe 8 is slidably guided in a guiding member, so that between the probe 8 and the guiding member a narrow liquid flow-through slit 10 remains, which at the proximal end runs into a liquid supply channel 11 surrounding the probe 8. The liquid is supplied at the entrance connection piece 19.

The endoscopic high speed injection device shown in FIGS. 2 to 4 can be used for applications with which liquids are to be injected and applied, respectively, without a needle, at locations which are difficult to access. The main application field can to be regarded as the field of medicine with minimally invasive operating techniques. Particularly, the drug treatment of the prostate using alpha blockers is considered. Further conceivable application fields are the drug treatment of tumors, or also the injection of substances through cellular membranes for gene therapy. However, one of skill in the art will recognize that many further application possibilities exist.

The endoscopic ejection apparatus is similar to a miniaturized jet vaccinator, the compression generating mechanism of which is disposed rather remote of the ejection opening 2. For example, the diameter of the guiding member 9 can approximately amount to 6 mm, and the diameter of the probe 8 can amount to approximately 2 to 3.5 mm. The volume of the liquid within the pressure chamber 1 is pressurized by means of the elastic excursion of the probe 8. Thereby for a short instance very elevated pressures occur (approximately 50 MPa), which result in a liquid ejection through the ejection opening.

The pressure energy is made available by means of the pneumatically accelerated driving piston 4 (FIG. 1) which strikes on the probe head 14 at the end of the accelerator pipe 12. Thereby, a compression wave is generated in the probe 8, which propagates along the probe 8. When the compression wave reaches the end of the probe 8, the liquid volume within the pressure chamber 1 is decreased by the progressive movement of the probe 8. This results in a pressure increase in the liquid. Thereafter, as a result of the pressure increase, liquid is ejected at a high velocity from the ejection opening 2 laterally disposed in the pressure chamber.

The liquid supply channel 11 permits a continuous operation of the ejector. At the entrance connection piece 19, the liquid is supplied at a low pressure (for example hydrostatically). Between the probe 8 and the guiding member 9, the liquid can flow to the pressure chamber via the narrow liquid flow-through slit 10.

The liquid supply to the pressure chamber 1 has to be controlled by means of a mechanical or hydraulic entrance valve, which, on the one hand, permits a liquid to be supplied to the pressure chamber between the compression processes, but, on the other hand, closes or is substantially blocked during the compression process, so that the pressure can be built-up. In the shown embodiment, this is achieved by means of the elongated flow-through slit 10 between the probe 8 and the guiding member 9. The flow-through slit 10 functions as a valve, because processes of pressurizing and refilling last different periods of time. The refilling of the pressure chamber 1 can always take place when the pressure in the pressure chamber 1 is not increased. By selecting appropriate dimensions of the nozzle opening and the pressure chamber, the pressure excess lasts for from 50 microseconds to 1 ms. Consequently, with a shot frequency limited by the acceleration process of the driving piston 4, (for example 20 Hz), a relatively long time remains, so that at a low pressure difference, a sufficient amount of liquid can be transported even through a very narrow flow-through slit 10. On the other hand, during the short duration compression, only a minimum amount of liquid can escape through the elongate narrow flow-through slit, whereby the maximum pressure increase which can be obtained is hardly decreased. The slit has the effect of a non stationary seal.

After the pressure increase in the pressure chamber 1, the pressure decreases to a value lower than the ambient pressure for a short time period. As a result, in an application in which the ejection opening 2 is not surrounded by liquid, ambient air is sucked in. If the sucked air cannot be displaced by means of the further supplied liquid, and removed from the pressure chamber before the next compression process begins, the instrument has to be deaerated. Therefore, a valve device is preferably provided, so that the ejection apparatus can be used in a gaseous environment as well as in a liquid environment. FIG. 3 shows a slide valve 18 slidably movable by means of the compression pressure. The slide valve 18 opens or closes the ejection opening 2. A further proposal is shown in FIG. 4. In order to keep the mass to be moved in the short control periods as low as possible, the wall of the pressure chamber 1 is formed as an elastic membrane 6, in which the ejection opening 2 is also disposed. The ejection opening 2 is closed by means of the free end of a pin 7. By means of the pressure increase in the pressure chamber 1, the elastic membrane 6 is lifted off the free end of the sealing pin 7 and a small slit occurs. Now, the liquid is enabled to flow through said slit into the ejection opening 2 and to get to the exterior.

The amount of liquid ejected per shot is less than 5 microliters because of the short compression time periods of the elastic wave. Conventional pistols output a liquid volume which is 300 to 1000 times higher.

The endoscopic ejection apparatus according to the invention particularly shows the following advantages:

very good dosing of the injection volume by means of a minimum output quantity per shot;

homogeneous distribution in the tissue of even very small volumes;

high penetration depth of the liquid to be injected;

minimum tissue injury;

high shot frequency of the particular injections achieved by means of an automatic refill mechanism (presently 20 shots per second can be achieved);

very short lasting steep compression in consequence of impulse transmission.

While according to the FIGS. 2 to 4 the ejection opening 2 is formed laterally with respect to the probe head, FIG. 5 shows an embodiment according to which the ejection opening 2 has its exit at the front side of the probe. In the embodiment of FIG. 5 the ejection channel is formed as a tapering, funnel-shaped nozzle.

In FIG. 6, a further embodiment of the invention in the shape of an inoculation device without a needle is illustrated. Here, a short working piston 3 is provided instead of the elongated probe 8 of the embodiments according to the FIGS. 2 to 5. The ejection opening 2 is controlled by a needle valve whose valve spring 20 has an elastic force which is adjustable by means of a hand wheel 21. The pressure chamber 1 is delimited by an adjusting piston 22 which can be adjusted for changing the volume received by the pressure chamber 1 by means of a second hand wheel 23 having an adjusting spindle 24.

The driving part according to FIG. 1 can serve as the driving part in this embodiment, wherein the outer pipe 25 of the driving part is being screwed to the device connection piece 26 which accommodates the working piston 4 instead of being screwed to the probe guide, so that the accelerator pipe 12 is in alignment with the working piston 3.

In the embodiment according to FIG. 6, the driving piston 4 is also pneumatically accelerated in the accelerator pipe 12 until the driving piston 4 strikes the working piston 3 (first impact). Since this impact does not take place completely elastically, only a portion (close to 100%) of the kinetic energy is transmitted to the working piston 3. If a completely elastic impact took place, the driving piston 4 would come to rest after the impact and the working piston would move on having the velocity of the driving piston 4 (under the assumption that the two pistons have the same masses and the same lengths). However, since a small portion of the energy gets lost during the impact, both pistons 3, 4 move on in the direction towards the valve needle 27, wherein, however, the driving piston 4 has a much lower velocity. The acceleration of the working piston 3 takes place within the time period, which the elastic waves need in the material of the pistons, to propagate once through the piston and back again. This time period is very short (with pistons of a length of 20 mm, approximately 8 ms) compared to the time period of the injection. The acoustic wave periods in the liquid volume which is pressurized last less than the time period of the injection (with a maximum piston length of 15 mm and water as the liquid: 10 ms). Therefore the liquid volume is homogeneously pressurized as a whole by means of the movement of the working piston 3. The pressure increase causes the working piston 3 to be steadily braked and later on reverse direction. The kinetic energy is converted to pressure energy and vice versa.

After the liquid is ejected, the working piston 3 collides with the driving piston 4 for the second time. Then, the latter moves back in the accelerator pipe 12. The working piston 3 keeps a small velocity, which is sufficient for it to return to its initial position. The pressure controlled inflow valve (not shown) opens into inflow opening 28 which is unblocked by the working piston 3 in its rest position, since the pressure in the pressure chamber is now lower than the pressure in a reservoir (for example a syringe). Thereby the ejected amount is refilled.

The pressure increase in the pressure chamber 1 causes an increase of the force exerted on the shoulder of the valve needle 27. As soon as this pressure force exceeds the force exerted by the preloaded valve spring 20, the valve needle 27 lifts off, and the ejection process starts. As a consequence of the change of the direction of movement of the working piston 3, the pressure reaches a maximum value, and then decreases. When the pressure falls below the opening pressure, the ejection opening 2 is closed again by means of the valve needle 27, and the ejection process is terminated. By means of the remaining liquid pressure, the working piston is pushed into the rest position.

The opening pressure is adjusted by means of the tension of the valve spring 20. A small thread pitch (0.5 mm) in the adjusting screw 21 permits the adjusting of the opening pressure between 10 and 200 bar by one revolution. It may appear that the spring (spring constant for example 200 N/mm) is very large and stiff. However, this is advantageous so that the needle closes quick enough. It is true that a non rigid spring could generate the same force by means of a higher compression, however, since it is a question of a mass and spring system, the resonance frequency of the mass and spring system has to be chosen high enough so that the closing process is terminated before the pressure in the system falls under the ambient pressure. Otherwise, air would be suck through the ejection opening 2.

The cap 29 screwed to the exit connection piece and comprising the ejection opening 2 is provided as a separate part, on the one hand in order to facilitate the manufacturing and, on the other hand, in order to provide the possibility that ejection openings 2 of different sizes can be used. The size of the ejection opening determines to a considerable extent how much liquid is ejected. A doubling of the size of the opening would result in quadruple the ejection volume, without having a notable influence on the ejection pressure. However, since this possibility requires a change of design, it also is possible to vary the volume of the pressure chamber 1, whereby the ejection volume can also be modified, if only to a minor extent, but without a change of design.

For deaerating and filling the pressure chamber 1, the adjusting piston for adjusting the volume of the pressure chamber 1 is adjusted to its minimum volume. Slightly under the edge of the piston, the deaeration opening 30 is disposed, which, in the operating condition of the apparatus, is closed by means of a screw (not shown). This screw is loosened a bit. By means of a filling syringe at the inflow opening 28, the liquid is pushed into the pressure chamber 1. The inflow valve thus opens, namely in reaction to an excess pressure from outside (low pressure in the interior). Liquid is subsequently pushed in until liquid comes out at the deaeration opening 30. Then the screw at the deaeration opening 30 is fastened. By means of rotating the adjusting spindle 24 the desired total volume can now be refilled, this is because, by extracting the adjusting piston, a negative pressure is generated, and the inflow valve opens, so that liquid is sucked from the reservoir syringe. Therefore, a glass embodiment of the reservoir syringe should be used which is smooth running.

Since small leakages at the valve needle 27 as well as at the adjusting piston 22 have to be expected, a leakage collecting system 31 is provided.

On the right hand in FIG. 6, a pressure converter bore is provided which is not required for the operation of the apparatus, but is advantageous for carrying out function testings and for calibrating the adjustment screws. Therefore, with a normal operation a blind pin is to be used to close the opening.

As already mentioned, the volume of the pressure chamber 1 can be altered by means of the adjusting piston 22. Both thereby and by the change of the velocity of the driving piston 4, the ejection pressure and the ejection volume can be changed. An increase of the velocity of the driving piston 4 in consequence of an increase of the pneumatic driving pressure causes an increase of both the ejection pressure and the ejection volume. The maximum value in the course an ejection is essentially directly proportional to the piston velocity. According to a first approximation, the ejection volume increases with the square root of the piston velocity. Therefore, by decreasing the volume of the pressure chamber 1 and increasing the velocity of the driving piston the ejection pressure can be increased, to at least partly compensate for the increase of the ejection volume also resulting from the increase of the piston velocity. If the volume of the pressurized liquid is increased while the piston velocity is kept constant, the ejection pressure is decreased and the ejection period is extended.

We claim:

1. Ejection apparatus for the high pressure ejection of a liquid, comprising:

(a) a pressure chamber for containing the liquid;

(b) an ejection opening communicating between an outside and an inside of the pressure chamber;

(c) a working piston displaceable in the pressure chamber from a first position at a beginning of a working stroke to second position at an end of the working stroke, having (1) a first end defining a first volume within the pressure chamber when the working piston is at the first position and displacing a second volume when the working piston moves from the first position to the second position, the first volume being substantially larger than the second volume, and (2) having a second end distal from the first end; and (d) a drive for driving the working piston including (1) an impact member for elastically impacting the second end of the working piston to cause the working piston to move from the first to the second position, and (2) means for accelerating the impact member to impact the working piston, wherein the impact member is not driven after an elastic impact with the working piston.

2. An ejection apparatus according to claim 1, wherein said impact member comprises a driving piston coaxial with said working piston and displaceable in a driving pipe.

3. An ejection apparatus according to claim 1, wherein said means for accelerating is pneumatic.

4. An ejection apparatus according to claim 1, wherein said means for accelerating is hydraulic.

5. An ejection apparatus according to claim 1, wherein said means for accelerating is mechanical.

6. An ejection apparatus according to claim 1, wherein said means for accelerating is electromagnetic.

7. An ejection apparatus according to claim 1, wherein said means for accelerating is electrostrictive.

8. An ejection apparatus according to claim 1, wherein said means for accelerating is piezo-electric.

9. An ejection apparatus according to claim 1, wherein said means for accelerating is thermal.

10. An ejection apparatus according to claim 1, wherein said means for accelerating operates to periodically accelerate said impact member, and said working piston returns to its first position after impact from said impact member.

11. An ejection apparatus according to claim 1, further comprising a valve for controlling said ejection opening.

12. An ejection apparatus according to claim 11, wherein said valve opens and closes according to pressure in the pressure chamber.

13. An ejection apparatus according to claim 12, wherein said valve comprises an elastic membrane defining a portion of a boundary of said pressure chamber and having a hole therein, and a sealing pin sealing said hole up to a predetermined pressure of said pressure chamber.

14. An ejection apparatus according to claim 1, comprising a plurality of ejection openings communicating between the outside and the inside of the pressure chamber.

15. An ejection apparatus according to claim 1, further comprising an inflow valve which opens to the pressure chamber when pressure in the chamber decreases.

16. An ejection apparatus according to claim 1, wherein the pressure chamber has an adjustable first volume.

17. An ejection apparatus according to claim 1, wherein said working piston comprises a portion of a probe of an endoscopic device.

18. An ejection apparatus according to claim 17, further comprising a liquid reservoir and a channel connecting the liquid reservoir with the pressure chamber.

19. An ejection apparatus according to claim 18, wherein said probe further comprises an end section adjacent the pressure chamber, a guiding member for slidably guiding the working piston, and a liquid flow through slit connecting the pressure chamber with the channel, wherein the channel extends along a length of the probe.

20. An ejection apparatus according to claim 17, further comprising an endoscopic catheter.

21. An ejection apparatus according to claim 12, wherein said apparatus is constructed to function as a needleless inoculation device, and said valve is constructed to have an adjustable opening pressure.

22. An ejection apparatus according to claim 1, wherein a ratio of the first volume to the second volume is from about 5:1 to about 20:1.

23. An ejection apparatus according to claim 1, wherein a ratio of the first volume to the second volume is about 5:1.

24. An ejection apparatus according to claim 1, wherein a ratio of the first volume to the second volume is about 20:1.

25. An ejection apparatus according to claim 10, wherein a ratio of the first volume to the second volume is from about 5:1 to about 20:1.

26. An ejection apparatus according to claim 11, wherein a ratio of the first volume to the second volume is from about 5:1 to about 20:1.

27. An ejection apparatus according to claim 15, wherein a ratio of the first volume to the second volume is from about 5:1 to about 20:1.

28. An ejection apparatus according to claim 17, wherein a ratio of the first volume to the second volume is from about 5:1 to about 20:1.

* * * * *